(12) United States Patent
Jeppesen et al.

(10) Patent No.: US 6,720,342 B2
(45) Date of Patent: Apr. 13, 2004

(54) HETEROCYCLIC COMPOUNDS AND THEIR PREPARATION AND USE

(75) Inventors: Lone Jeppesen, Virum (DK); Per Sauerberg, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/940,963

(22) Filed: Aug. 28, 2001

(65) Prior Publication Data

US 2002/0115697 A1 Aug. 22, 2002

Related U.S. Application Data

(63) Continuation of application No. 09/613,656, filed on Jul. 11, 2000, now abandoned, which is a continuation of application No. 09/148,637, filed on Sep. 4, 1998, now abandoned, which is a continuation of application No. PCT/DK97/00120, filed on Mar. 19, 1997.

(30) Foreign Application Priority Data

Mar. 19, 1996 (DK) ................................................ 322/96

(51) Int. Cl.$^7$ ..................... C07D 285/10; A61K 31/423

(52) U.S. Cl. ........................................ 514/362; 548/135
(58) Field of Search ........................... 514/362; 548/135

(56) References Cited

U.S. PATENT DOCUMENTS 5,821,371 A * 10/1998 Alt .............................. 548/135

FOREIGN PATENT DOCUMENTS

| EP | 0 709 381 | 5/1996 |
| EP | 0 745 601 | 12/1996 |
| WO | WO 92/03433 | 3/1992 |
| WO | WO 95/17180 | 6/1995 |

* cited by examiner

Primary Examiner—Robert Gerstl
(74) Attorney, Agent, or Firm—Rosemarie R. Wilk-Orescan; Reza Green

(57) ABSTRACT

The present invention relates to therapeutically active azabicyclic compounds, a method of preparing the same and to pharmaceutical or veterinary compositions comprising the compounds. The novel compounds are useful in treating a disease in the central nervous system caused by malfunctioning of the muscarinic cholinergic system.

10 Claims, No Drawings

HETEROCYCLIC COMPOUNDS AND THEIR PREPARATION AND USE

CROSS-REFERENCE TO RELATED APPLICATIONS

This application is a continuation of application Ser. No. 09/613,656 filed Jul. 11, 2000 now abandoned, which in a continuation of application Ser. No. 09/148,637 filed Sep. 4, 1998, now abandoned, which is a continuation application of PCT/DK97/00120 filed Mar. 19, 1997 and claims priority under 35 U.S.C. 119 of Danish application 0322/96 filed Mar. 19, 1996, the contents of which are fully incorporated herein by reference.

FIELD OF THE INVENTION

The present invention relates to therapeutically active azabicyclic compounds, a method of preparing the same and to pharmaceutical or veterinary compositions comprising the compounds. The novel compounds are useful in treating a disease in the central nervous system caused by malfunctioning of the muscarinic cholinergic system.

BACKGROUND OF THE INVENTION

Due to the generally improved health situation in the western world, elderly-related diseases are much more common now than in the past and are likely to be even more common in the future.

One of the elderly-related symptoms is a reduction of the cognitive functions. This symptom is especially pronounced in the pathophysiological disease known as Alzheimer's disease. This disease is combined with, and also most likely caused by, an up to 90% degeneration of the cholinergic neurons in nucleus basalis, which is part of substantia innominata. These neurons project to the pre-frontal cortex and hippocampus and have a general stimulatory effect on the cognitive functions of the forebrain as well as of hippocampus, namely learning, association, consolidation, and recognition.

It is a characteristic of Alzheimer's disease that although the cholinergic neurons degenerate, the postsynaptic muscarinic receptors in the forebrain and hippocampus still exist. Therefore, muscarinic cholinergic agonists are useful in the treatment of Alzheimer's disease, in halting progression of Alzheimer's disease, and in improving the cognitive functions of elderly people.

The compounds of this invention are also useful analgesic agents and therefore useful in the treatment of severe painful conditions.

Furthermore, the compounds of this invention are useful in the treatment of glaucoma, psychosis, mania, bipolar disorder, schizophrenia or schizophreniform conditions, depression, bladder dysfunctions, anxiety, sleeping disorders, epilepsy, cerebral ischemia and gastrointestinal motility disorders.

SUMMARY OF THE INVENTION

It is an object of the invention to provide new muscarinic cholinergic compounds.

The novel compounds of the invention are heterocyclic compounds having formula I

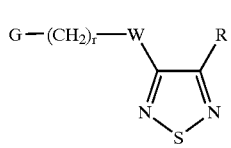

wherein W is oxygen or sulphur; R is selected from the group consisting of hydrogen, amino, halogen, $NHR^6$, $NR^6R^7$, $R^4$, $-OR^4$, $-SR^4$, $-SOR^4$, $-SO_2R^4$, $C_{3-10}$-cycloalkyl, $C_{4-12}$-(cycloalkylalkyl), $-Z-C_{3-10}$-cycloalkyl and $-Z-C_{4-12}$-(cycloalkylalkyl) which is optionally substituted with $C_{1-6}$-alkyl; $R^4$ is selected from the group consisting of $C_{1-15}$-alkyl, $C_{2-15}$-alkenyl, $C_{2-15}$-alkynyl and $C_{4-15}$-alkenynyl, each of which is optionally substituted with one or more independently selected from the group consisting of halogen(s), $-CF_3$, $-CN$, Y, phenyl and phenoxy wherein phenyl or phenoxy is optionally substituted with one or more independently selected from the group consisting of $-OH$, halogen, $-NO_2$, $-CN$, $C_{1-4}$-alkyl, $C_{1-4}$-alkylthio, $C_{1-4}$-alkoxy, $-SCF_3$, $-OCF_3$, $-CF_3$, $-CONH_2$ and $-CSNH_2$; or R is phenyl or benzyloxycarbonyl, each of which is optionally substituted with one or more independently selected from the group consisting of halogen, $-CN$, $C_{1-4}$-alkyl, $C_{1-4}$-alkoxy, $-OCF_3$, $-CF_3$, $-CONH_2$ and $-CSNH_2$; or R is selected from the group consisting of $-OR^5Y$, $-SR^5Y$, $OR^5ZY$, $-SR^5ZY$, $-OR^5ZR^4$ and $-SR^5ZR^4$; Z is oxygen or sulphur; $R^5$ is $C_{1-15}$-alkylene, $C_{2-15}$-alkenylene, $C_{2-15}$-alkynylene or $C_{4-15}$-alkenynylene; Y is a 5 or 6 membered heterocyclic group optionally substituted with one or more independently selected from the group consisting of $-OH$, halogen, $-NO_2$, $-CN$, $C_{1-14}$-alkyl, $C_{1-4}$-alkylthio, $C_{1-4}$-alkoxy, $-SCF_3$, $-OCF_3$, $-CF_3$, $-CONH_2$ and $-CSNH_2$; G is

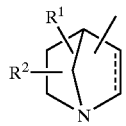

$R^6$ and $R^7$ independently are selected from the group consisting of hydrogen and $C_{1-6}$-alkyl; or $R^6$ and $R^7$ together with the nitrogen atom optionally form a 4- to 6-membered ring; $R^1$ and $R^2$ independently are selected from the group consisting of hydrogen, $-OH$, $=O$, $C_{1-15}$-alkyl, $C_{2-15}$-alkenyl, $C_{2-15}$-alkynyl, $C_{1-10}$-alkoxy, and $C_{1-5}$-alkyl substituted with one or more independently selected from the group consisting of $-OH$, $-COR^8$, $-CH_2OH$, halogen, $-NH_2$, carboxy and phenyl; $R^8$ is hydrogen, $C_{1-8}$-alkyl; r is 0, 1 or 2; --- is a single or double bond; or a pharmaceutically acceptable salt or solvate thereof.

As used herein, the term "halogen" means Cl, Br, F, and I. Especially preferred halogens include Cl, Br, and F.

The terms "$C_{1-n'}$-alkyl" wherein n' can be from 2 through 15, as used herein, represent a branched or linear alkyl group having from one to the specified number of carbon atoms. Typical $C_{1-6}$-alkyl groups include, but are not limited to, methyl, ethyl, n-propyl, iso-propyl, butyl, iso-butyl, sec-butyl, tert-butyl, pentyl, hexyl and the like.

The terms "$C_{2-n'}$-alkenyl" wherein n' can be from 3 through 15, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The terms "$C_{2-n'}$-alkynyl" wherein n' can be from 3 through 15, as used herein, represent an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, 2-pentynyl and the like.

The terms "$C_{4-n'}$-alkenynyl" wherein n' can be from 5 through 15, as used herein, represent an unsaturated branched or linear hydrocarbon group having from 4 to the specified number of carbon atoms and both at least one double bond and at least one triple bond. Examples of such groups include, but are not limited to, 1-penten-4-yne, 3-penten-1-yne, 1,3-hexadiene-5-yne and the like.

The term "$C_{3-n}$-cycloalkyl" wherein n=4–10, as used herein, represents e.g. cyclopropyl, cyclobutyl, cyclopentyl, cyclohexyl, cycloheptyl and cyclooctyl and the like.

As used herein the term $C_{4-12}$-(cycloalkylalkyl) represents a branched or linear alkyl group substituted at a terminal carbon with a cycloalkyl group. Typical cycloalkylalkyl groups include cyclopropylethyl, cyclobutylmethyl, cyclohexylethyl, cyclohexylmethyl, 3-cyclopentylpropyl, and the like.

As used herein, the term "$C_{1-4}$-alkoxy" represents methoxy, ethoxy, propoxy, butoxy and the like.

As used herein, the phrase "one or more selected from" shall more preferably refer to from 1–3 substituents. The term shall further preferably refer to from 1–2 substituents.

As used herein, the phrase "5 or 6 membered heterocyclic group" means a group containing from one to four N, O or S atom(s) or a combination thereof, which heterocyclic group is optionally substituted at carbon or nitrogen atom(s) with —OH, halogen, —$NO_2$, —CN, $C_{1-4}$-alkyl, $C_{1-4}$-alkylthio, $C_{1-4}$-alkoxy, —$SCF_3$, —$OCF_3$, —$CF_3$, —$CONH_2$ and —$CSNH_2$, or a carbon atom in the heterocyclic group together with an oxygen atom form a carbonyl group, or which heterocyclic group is optionally fused with a phenyl group. The phrase "5 or 6 membered heterocyclic group" includes, but is not limited to, 5-membered heterocycles having one hetero atom (e.g. thiophenes, pyrroles, furans); 5-membered heterocycles having two heteroatoms in 1,2 or 1,3 positions (e.g. oxazoles, pyrazoles, imidazoles, thiazoles, purines); 5-membered heterocycles having three heteroatoms (e.g. triazoles, thiadiazoles); 5-membered heterocycles having four heteroatoms; 6-membered heterocycles with one heteroatom (e.g. pyridine, quinoline, isoquinoline, phenanthridine, cyclohepta[b]pyridine); 6-membered heterocycles with two heteroatoms (e.g. pyridazines, cinnolines, phthalazines, pyrazines, pyrimidines, quinazolines); 6-membered heterocycles with three heteroatoms (e.g. 1,3,5-triazine); and 6-membered heterocycles with four heteroatoms.

As used herein with reference to the G substituent, the —$(CH_2)_r$-W-thiadiazole moiety can be attached at any carbon atom of the azabicyclic ring. Further, $R^1$ and $R^2$ of the G substituent may be present at any position, including the point of attachment of the —$(CH_2)_r$-W-thiadiazole moiety.

As used herein the phrase "$R^6$ and $R^7$ together with the nitrogen atom optionally form a 4- to 6-member ring" means that $R^6$ and $R^7$ are each independently hydrogen, $C_{1-5}$-alkyl wherein the $R^8$ and $R^7$ groups may optionally join to form a 4- to 6-member ring including the nitrogen. For example, optionally joined groups include, but are not limited to:

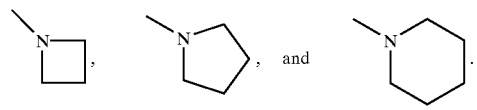

As used herein the term "carboxy" refers to a substituent having the common meaning understood by the skilled artisan, wherein the point of attachment may be through the carbon or oxygen atom of the group.

As used herein, the term "alkoxide metal" means a metal suitable for alkoxide formation. Such alkoxide metals include, but are not limited to, $Li^+$, $K^+$, $Na^+$, $Cs^+$, and $Ca^{++}$. Especially preferred alkoxide metals include $Li^+$, $K^+$, and $Na^+$.

In a preferred embodiment, the present invention is concerned with compounds of formula I wherein G is saturated.

In another preferred embodiment, the present invention is concerned with compounds of formula I wherein G is

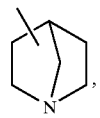

(G)

and wherein the —$(CH_2)_r$—W-thiadiazole is attached to the 3- or 4-position of G.

In another preferred embodiment, the present invention is concerned with compounds of formula I wherein G is

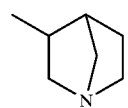

(G)

In another preferred embodiment, the present invention is concerned with compounds of formula I wherein r is 0.

In another preferred embodiment, the present invention is concerned with compounds of formula I wherein W is oxygen.

In another preferred embodiment, the present invention is concerned with compounds of formula I wherein R is —$OR^4$, —$SR^4$, —$SOR^4$, —$SO_2R^4$, —Z—$C_{3-10}$-cycloalkyl or —Z—$C_{4-12}$-(cycloalkylalkyl) which is optionally substituted with $C_{1-6}$-alkyl or R is —$OR^5Y$, —$SR^5Y$, —$OR^5ZY$, —$SR^5ZY$, —$OR^5ZR^4$ or —$SR^5ZR^4$, preferably R is —$OR^4$, —$SR^4$, —$OR^5ZY$, —$SR^5ZY$, —$OR^5ZR^4$ or —$SR^5ZR^4$.

In another preferred embodiment, the present invention is concerned with compounds of formula I wherein $R^4$ is $C_{1-15}$-alkyl, $C_{2-15}$-alkenyl, $C_{2-15}$-alkynyl or $C_{4-15}$-alkenynyl, each of which is optionally substituted with one or more independently selected from the group consisting of halogen (s), —$CF_3$, —CN, Y and phenyl which is optionally substituted with one or more independently selected from the group consisting of —OH, halogen, —CN, $C_{1-4}$-alkyl, $C_{1-14}$-alkylthio, $C_{1-4}$-alkoxy, —$SCF_3$, —$OCF_3$, and $CF_3$.

In another preferred embodiment, the present invention is concerned with compounds of formula I wherein R is —$OR^4$ or —$SR^4$, wherein $R^4$ is straight or branched $C_{2-8}$-alkynyl, preferably propynyl, substituted with phenyl or Y, preferably Y is thiophene, pyridine, furan or thiazole, each of which is optionally substituted with —OH, halogen, —$NO_2$, —CN, $C_{1-4}$-alkyl, $C_{1-4}$-alkylthio, $C_{1-4}$-alkoxy, —$SCF_3$, —$OCF_3$, —$CF_3$, —$CONH_2$ or —$CSNH_2$, preferably halogen, —CN, $C_{1-4}$-alkoxy or —$OCF_3$.

It is to be understood that the invention extends to each of any of the stereoisomeric forms of the compounds of the present invention as well as the pure diastereomeric, pure enantiomeric, and racemic forms of the compounds of this invention.

The starting materials for the illustrated process are, if nothing else mentioned, commercially available or may be prepared using methods known to the skilled artisan.

The invention also relates to methods of preparing the above mentioned compounds, comprising a) reacting a compound of formula II

NC—CN  (II)

with first $HSR^4/Et_2NH$ and subsequently $S_2Hal_2$, wherein $R^4$ has the meaning defined above, to form a compound of formula III

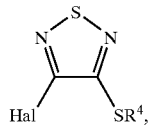

(III)

wherein R has the meaning defined above; or the compound of formula II is first reacted with $HOR^4/Et_3N$ and subsequently with $S_2Hal_2$, wherein $R^4$ has the meaning defined above, to form a compound of formula IV

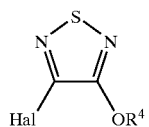

(IV)

wherein $R^4$ has the meaning defined above; and a compound of formula III or formula IV can subsequently be reacted in the presence of an alkoxide metal with a compound of formula V G—(CH$_2$)$_r$—W—H  (V)

wherein G, r and W have the meanings defined above, to form a compound of formula VI selected from the following

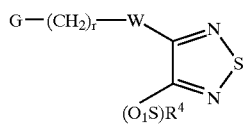

(VI)

wherein G, R, W and $R^4$ have the meanings defined above; or b) a compound of formula III can be oxidized to form a compound of formula VII

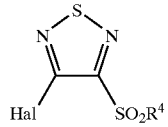

(VII)

wherein $R^4$ has the meaning defined above, which subsequently can be reacted with a compound of formula V to form a compound of formula VIII

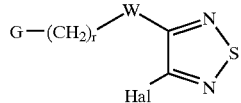

(VIII)

wherein G, r and W have the meanings defined above which compound can subsequently be reacted with either R—OH or RMgHal to form a compound of formula I; or c) a compound of formula VI

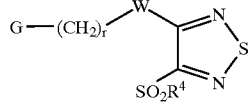

(VI)

wherein G, r, W and $R^4$ have the meanings defined above, can be oxidized to form a compound of formula IX

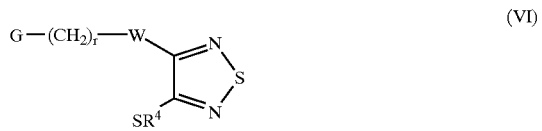

(IX)

wherein G, r, W and $R^4$ have the meanings defined above which compound subsequently can be reacted with either R—OH or RMgHal to form a compound of formula I.

The term "Hal" refers to Cl or Br. Preferred oxidizing agents for the process include oxone and sodiumperiodate. Oxone is an especially preferred oxidizing agent.

As is always the case in chemistry, the rate of the reaction depends on a variety of factors, such as the temperature and the exact compound which is to be prepared. The course of the reaction may be followed using methods such as thin layer chromatography (TLC), high performance liquid chromatography (HPLC), gas chromatography (GC) and nuclear magnetic resonance spectroscopy (NMR) to detect the degree of completion of the reaction. The operator may obtain maximum yields using the process by extending the reaction time. Alternatively, the operator may wish to obtain maximum throughput by cutting off the reaction at the point at which it reaches an economical degree of completion.

When the product of a step in the following process is an oil, it may be isolated by standard methods. Such methods include distillation, flash chromatography, HPLC and the like.

The invention further provides a formulation comprising a compound of formula I and one or more pharmaceutically acceptable diluents, carriers or excipients therefor.

The invention provides a method for treating a condition associated with a malfunction of the cholinergic muscarinic receptor system. Such conditions which may be treated using a compound of this invention include, but are not limited to Alzheimer's Disease, cognitive dysfunction, severely painful conditions, glaucoma, psychosis, schizophrenia, bladder dysfunction, anxiety, sleep disorders, and other such conditions associated with the modulation of a muscarinic receptor.

As used herein the term "treating" includes prophylaxis of a physical and/or mental condition or amelioration or elimination of the developed physical and/or mental condition once it has been estabished or alleviation of the characteristic symptoms of such condition.

As used herein the term "malfunctioning of the muscarinic cholinergic system" shall have the meaning accepted by the skilled artisan. For example the term shall refer to, but is not in any way limited to conditions such as glaucoma, psychosis, schizophrenia or schizophreniform conditions, depression, sleeping disorders, epilepsy and gastrointestinal motility disorders. Other such conditions include Alzheimer's disease and incontinence.

As used herein the phrase "interacting with a muscarinic cholinergic receptor" shall include compounds which block muscarinic cholinergic receptors or modulate such receptors. The phrase shall include the effect observed when compounds act as agonists, partial agonists and/or antagonists at a muscarinic cholinergic receptor.

Examples of pharmaceutically acceptable salts include inorganic and organic acid addition salts such as hydrochloride, hydrobromide, sulphate, phosphate, acetate, fumarate, maleate, citrate, lactate, tartrate, oxalate, or similar pharmaceutically acceptable inorganic or organic acid addition salts, and include the pharmaceutically acceptable salts listed in *Journal of Pharmaceutical Science*, 66, 2 (1977) which are known to the skilled artisan. The compounds of this invention may form solvates with standard low molecular weight solvents using methods known to the skilled artisan.

The pharmacological properties of the compounds of the invention can be illustrated by determining their capability to inhibit the specific binding of $^3$H-Oxotremorine-M ($^3$H-Oxo). Birdsall N. J. M., Hulme E. C., and Burgen A. S. V. (1980). "The Character of Muscarinic Receptors in Different Regions of the Rat Brain". Proc. Roy. Soc. London (Series B) 207, 1.

$^3$H-Oxo labels muscarinic receptor in the CNS (with a preference for agonist domains of the receptors). Three different sites are labelled by $^3$H-Oxo. These sites have affinity of 1.8, 20 and 3000 nM, respectively. Using the present experimental conditions only the high and medium affinity sites are determined.

The inhibitory effects of compounds on $^3$H-Oxo binding reflects the affinity for muscarinic acetylcholine receptors.

All preparations are performed at 0–4° C. unless otherwise indicated. Fresh cortex (0.1–1 g) from male Wistar rats (150–250 g) is homogenized for 5–10 s in 10 ml 20 mM Hepes pH: 7.4, with an Ultra-Turrax homogenizer. The homogenizer is rinsed with 10 ml of buffer and the combined suspension centrifuged for 15 min. at 40,000×g. The pellet is washed three times with buffer. In each step the pellet is homogenized as before in 2×10 ml of buffer and centrifuged for 10 min. at 40,000×g.

The final pellet is homogenized in 20 mM Hepes pH: 7.4 (100 ml per g of original tissue) and used for binding assay. Aliquots of 0.5 ml is added 25 µl of test solution and 25 µl of $^3$H-Oxotremorine (1.0 nM, final concentration) mixed and incubated for 30 min. at 25° C. Non-specific binding is determined in triplicate using arecoline (1 µg/ml, final concentration) as the test substance. After incubation samples are added 5 ml of ice-cold buffer and poured directly onto Whatman GF/C glass fiber filters under suction and immediately washed 2 times with 5 ml of ice-cold buffer. The amount of radioactivity on the filters are determined by conventional liquid scintillation counting. Specific binding is total binding minus non specific binding.

Test substances are dissolved in 10 ml water (if necessary heated on a steambath for less than 5 min.) at a concentration of 2.2 mg/ml. 25–75% inhibition of specific binding must be obtained before calculation of $IC_{50}$.

The test value will be given as $IC_{50}$ (the concentration (nM) of the test substance which inhibits the specific binding of $^3$H-Oxo by 50%).

$$IC_{50} = \text{(applied test substance concentration)} \times (C_x/C_o - C_x) nM$$

where $C_o$ is specific binding in control assays and $C_x$ is the specific binding in the test assay. (The calculations assume normal mass-action kinetics).

Furthermore the pharmacological properties of the compounds of the invention can also be illustrated by determining their capability to inhibit $^3$H-PRZ (pirenzepine, [N-methyl-$^3$H]) binding to rat cerebral cortex membranes. Pirenzepine binds selectively to subtype of muscarinic receptors. Historically the type is named the $M_1$-site, whereas pirenzepine sensitive site would be more appropriate. Although selective for $M_1$-sites pirenzepine also interact with $M_2$-sites.

All preparations are performed at 0–4° C. unless otherwise indicated. Fresh cortex (0.1–1 g) from male Wistar rats (150–200 g) is homogenized for 5–10 s. in 10 ml 20 mM Hepes pH: 7.4, with an Ultra-Turrax homogenizer. The homogenizer is rinsed with 2×10 ml of buffer and the combined suspension centrifuged for 15 min at 40,000×g. The pellet is washed three times with buffer. In each step the pellet is homogenized as before in 3×10 ml of buffer and centrifuged for 10 min at 40,000×g.

The final pellet is homogenized in 20 mM Hepes pH: 7.4 (100 ml per g of original tissue) and used for binding assay. Aliquots of 0.5 ml is added 20 µl of test solution and 25 µl of $^3$H-Pirenzepine (1.0 nM, final conc.), mixed and incubated for 60 min at 20° C. Non-specific binding is determined in triplicate using atropine (1 µg/ml, final conc.) as the test substance. After incubation samples are added 5 ml of ice-cold buffer and poured directly onto Whatman GF/C glass fiber filters under suction and immediately washed 2 times with 5 ml of ice-cold buffer. The amount of radioactivity on the filters are determined by conventional liquid scintillation counting. Specific binding is total binding minus non-specific binding.

Test substances are dissolved in 10 ml water, at a concentration of 0.22 mg/ml. 25–75% inhibition of specific binding must be obtained before calculation of $IC_{50}$.

The test value will be given as $IC_{50}$ (the concentration (nM) of the test substance which inhibits the specific binding of $^3$H-PRZ by 50%).

$$IC_{50} = \text{(applied test substance concentration)} \times (C_x/C_o - C_x) nM$$

where $C_o$ is specific binding in control assays and $C_x$ is the specific binding in the test assay. (The calculations assume normal mass-action kinetics).

Test results obtained by testing some compounds of the present invention will appear from the following table 1:

TABLE 1

| Compound | $^3$H-Oxo $IC_{50}$, nM | $^3$H-PRZ $IC_{50}$, nM |
|---|---|---|
| 1 | 1.6 | 0.14 |
| 2 | 1.4 | 4.2 |
| 4 | 7.9 | 8.3 |
| 5 | 10 | 14 |
| 6 |  | 17 |
| 7 | 10 | 24 |
| 8 | 4.9 | 9.8 |
| 9 | 25 | 30 |
| 10 | 5.3 | 20 |
| 11 | 2.1 | 23 |
| 12 | 3.7 | 29 |
| 13 | 4.3 | 44 |
| 14 | 49 | 32 |
| 15 | 18 | 14 |
| 16 | 148 | 129 |
| 17 | 72 | 48 |
| 18 | 79 | 12 |
| 19 | 126 | 53 |
| 20 |  | 11 |
| 21 | 302 | 100 |
| 22 | 190 | 50 |
| 23 | 1.6 | 13 |
| 25 | 1.7 | 4.5 |
| 26 | 1.3 | 3.9 |
| 27 | 8.3 | 5.3 |
| 28 | 5.5 |  |
| 29 | 3.1 | 9.1 |
| 30 |  | 3.4 |
| 31 |  | 23 |
| 32 | 3.1 | 34 |
| 33 | 83 | 16 |
| 34 |  | 31 |
| 36 | 1.0 | 4.7 |
| 37 | 2.2 | 8.7 |
| 39 | 105 | 56 |
| 40 | 1.8 | 43 |
| 41 |  | 9.2 |

By testing the compounds of the present invention it is found that they inhibit the specific binding of $^3$H-Oxotremorine-M and $^3$H-Pirenzepine.

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients suffering from diseases in the central nervous system caused by malfunctioning of the muscarinic cholinergic system it may frequently be necessary to begin with a dosage of from about 20 to about 70 mg per day and when the condition is under control to reduce the dosage as low as from about 0.1 to about 10 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, depot, subcutaneous, intravenous, intraurethral, intramuscular, intranasal, ophthalmic solution or an ointment, the oral route being preferred.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by empolying procedures well known in the art.

The pharmaceutical preparations can be sterilized and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 0.1 to about 100 mg in a pharmaceutically acceptable carrier per unit dosage.

A typical tablet, appropriate for use in this method, may be prepared by conventional tabletting techniques and contains:

| | |
|---|---|
| Active compound | 5.0 mg |
| Lactosum | 67.8 mg Ph. Eur. |
| Avicel ® | 31.4 mg |
| Amberlite ® | 1.0 mg |
| Magnesii stearas | 0.25 mg Ph. Eur. |

The compounds according to this invention may be suitable for administration to an animal. Such animals include both domestic animals, for example livestock, laboratory animals, and household pets, and non-domestic animals such as wildlife. More preferably, the animal is a vertebrate. Most preferably, a compound according to this invention shall be administered to a mammal. It is especially preferred that the animal is a domestic mammal or a human. The most preferred mammal is a human. For such purposes, a compound of this invention may be administered as a feed additive or in bulk form.

The invention will now be described in further detail with reference to the following examples. The examples are provided for illustrative purposes, and are not to be construed as limiting the scope of the invention in any way.

EXAMPLE 1

Endo 3-(3-butylthio-1,2,5-thiadiazol-4-yloxy)-1-azabicyclo[2.2.1]heptane, oxalate A solution of endo 3-hydroxy-1-azabicyclo[2.2.1]heptane, (J.Med.Chem. 1992, 35, 2392–2406), (225 mg, 2.0 mmol) in dry THF (5 ml) was treated with 95% potassium t-butoxide (260 mg, 2.0 mmol). After 30 min., the reaction was cooled in ice-water. To the cold solution was added a single portion of 3-chloro-4-butylthio-1,2,5-thiadiazole (420 mg, 2.0 mmol). Cooling was removed and after 4 h the reaction was heated to reflux for 1.5 h. The solvent was evaporated and the residue suspended in cold water and acidified with 4N HCl. The mixture was extracted with ether (2×-discarded). The aqueous phase was made basic and the mixture extracted with dichloromethane (3×). The dichloromethane extracts were washed with water, dried ($MgSO_4$), and the solvent evaporated. The residue was taken up in acetone, and the product precipitated with oxalic acid in acetone followed by ether to give 240 mg (32%) of the title compound. M.p. 125–126° C. Compound 1.

EXAMPLE 2

The following compound was made in exactly the same manner as described in example 1 by using the reagents indicated.

Endo 3-(3-propylthio-1,2,5-thiadiazol-4-yloxy)-1-azabicyclo[2.2.1]heptane, oxalate from endo 3-hydroxy-1-azabicyclo[2.2.1]heptane and 3-chloro-4-propylthio-1,2,5-thiadiazole. Yield: 38%. M.p. 136–137° C. Compound 2.

EXAMPLE 3

Endo 3-(3-propylsulfonyl-1,2,5-thiadiazol-4-yloxy)-1-azabicyclo[2.2.1]heptane, oxalate A solution of endo 3-(3-propylthio-1,2,5-thiadiazol-4-yloxy)-1-azabicyclo-[2.2.1]heptane, oxalate (example 2) (4.1 g, 11.3 mmol) in water (30 ml) and 1N HCl (13.5 ml) was cooled in ice-water. Oxone (10.5 g, 17.1 mmol) in water (60 ml) was added to the reaction over 10 min. Cooling was removed and the reaction stirred for 16 h. The reaction was cooled in ice-water and then made basic with $NH_3$. The mixture was extracted with ether (6×). The extracts were dried ($MgSO_4$) and evaporated. The product was taken up in acetone and precipitated with oxalic acid in acetone to give 3.2 g (73%). M.p. 168–169° C. Compound 3.

EXAMPLE 4

Endo 3-(3-[3-(4-fluorophenyl)-2-propynyl-1-oxy]-1,2,5-thiadiazol-4-yloxy)-1-azabicyclo[2.2.1]heptane, oxalate A suspension of sodium hydride (90 mg, 3.0 mmol) in dry THF (30 ml) and 3-(4-fluorophenyl)-2-propyn-1-ol(225 mg, 1.5 mmol) was stirred at room temperature for 1 h under nitrogen. The reaction was then cooled in ice-water and added endo 3-(3-propylsulfonyl-1,2,5-thiadiazol-4-yloxy)-1-azabicyclo[2.2.1]heptane (example 3) (303 mg, 1.0 mmol). After 16 h the cold reaction was quenched with water and the product extracted with ether (3×). The extracts were dried ($MgSO_4$) and the solvent evaporated. The product was taken up in acetone and precipitated with oxalic acid in acetone followed by ether to give 180 mg (41%) of the title compound. M.p. 163–165° C. Compound 4.

EXAMPLE 5

The following compounds were made in exactly the same manner as described in example 4 by using the reagents indicated:

Endo 3-(3-[3-phenyl-2-propynyl-1-oxy]-1,2,5-thiadiazol-4-yloxy)-1-azabicyclo[2.2.1]heptane, oxalate from endo 3-(3-propylsulfonyl-1,2,5-thiadiazol-4-yloxy)-1-azabicyclo[2.2.1]heptane (example 3) and 3-phenyl-2-propyn-1-ol. Yield: 81%. M.p. 158–159° C. Compound 5.

Endo 3-(3-[3-(3-methoxyphenyl)-2-propynyl-1-oxy]-1,2,5-thiadiazol-4-yloxy)-1-azabicyclo[2.2.1]heptane, oxalate from endo 3-(3-propylsulfonyl-1,2,5-thiadiazol-4-yloxy)-1-azabicyclo[2.2.1]heptane (example 3) and 3-(3-methoxyphenyl)-2-propyn-1-ol. Yield: 47%. M.p. 142–143° C. Compound 6.

Endo 3-(3-[3-methyl-2-butenyl-1-oxy]-1,2,5-thiadiazol-4-yloxy)-1-azabicyclo[2.2.1]heptane, oxalate from endo 3-(3-propylsulfonyl-1,2,5-thiadiazol-4-yloxy)-1-azabicyclo[2.2.1]heptane (example 3) and 3-methyl-2-buten-1-ol. Yield: 55%. M.p. 112–115° C. Compound 7.

Endo 3-(3-[2-cyclopropylethyl-1-oxy]-1,2,5-thiadiazol-4-yloxy)-1-azabicyclo[2.2.1]heptane, oxalate from endo 3-(3-propylsulfonyl-1,2,5-thiadiazol-4-yloxy)-1-azabicyclo[2.2.1]heptane (example 3) and cyclopropylethanol. Yield: 74%. M.p. 132–133° C. Compound 8.

Endo 3-(3-[4-fluorobenzyloxy]-1,2,5-thiadiazol-4-yloxy)-1-azabicyclo-[2.2.1]heptane, oxalate from endo 3-(3-propylsulfonyl-1,2,5-thiadiazol-4-yloxy)-1-azabicyclo[2.2.1]heptane (example 3) and 4-fluorobenzylalcohol. Yield: 62% M.p. 144–145° C. Compound 9.

Endo 3-(3-[2-butenyl-1-oxy]-1,2,5-thiadiazol-4-yloxy)-1-azabicyclo[2.2.1]heptane, oxalate from endo 3-(3-propylsulfonyl-1,2,5-thiadiazol-4-yloxy)-1-azabicyclo[2.2.1]heptane (example 3) and crotyl alcohol. Yield: 67%. M.p. 129–131° C. Compound 10.

Endo 3-(3-[2-butynyl-1-oxy]-1,2,5-thiadiazol-4-yloxy)-1-azabicyclo[2.2.1]heptane, oxalate from endo 3-(3-propylsulfonyl-1,2,5-thiadiazol-4-yloxy)-1-azabicyclo[2.2.1]heptane (example 3) and 2-butyn-1-ol. Yield: 73%. M.p. 194–196° C. Compound 11.

Endo 3-(3-methylthioethoxy-1,2,5-thiadiazol-4-yloxy)-1-azabicyclo-[2.2.1]heptane, oxalate from endo 3-(3-propylsulfonyl-1,2,5-thiadiazol-4-yloxy)-1-azabicyclo[2.2.1]heptane (example 3) and 2-hydroxyethylmethyl sulfide. Yield: 60%. M.p. 117–119° C. Compound 12.

Endo 3-(3-methoxyethoxy-1,2,5-thiadiazol-4-yloxy)-1-azabicyclo[2.2.1]heptane, oxalate from endo 3-(3-propylsulfonyl-1,2,5-thiadiazol-4-yloxy)-1-azabicyclo[2.2.]heptane (example 3) and 2-methoxyethanol. Yield: 78%. M.p. 139–141° C. Compound 13.

Endo 3-(3-[4-trifluoromethoxybenzyloxy]-1,2,5-thiadiazol-4-yloxy)-1-azabicyclo[2.2.1]heptane, oxalate from endo 3-(3-propylsulfonyl-1,2,5-thiadiazol-4-yloxy)-1-azabicyclo[2.2.1]heptane (example 3) and 4-(trifluoromethoxy)benzyl alcohol. Yield: 77%. M.p. 116–119° C. Compound 14.

Endo 3-(3-[4,4,4-trifluorobutyl-1-oxy]-1,2,5-thiadiazol-4-yloxy)-1-azabicyclo[2.2.1]heptane, oxalate from endo 3-(3-propylsulfonyl-1,2,5-thiadiazol-4-yloxy)-1-azabicyclo[2.2.1]heptane (example 3) and 4,4,4-trifluorobutanol. Yield: 73%. M.p. 135–137° C. Compound 15.

Endo 3-(3-[2-fluoro-4-(trifluoromethyl)-benzyloxy]-1,2,5-thiadiazol-4-yloxy)-1-azabicyclo[2.2.1]heptane, oxalate from endo 3-(3-propylsulfonyl-1,2,5-thiadiazol-4-yloxy)-1-azabicyclo[2.2.1]heptane (example 3) and 2-fluoro-4-

(trifluoromethyl)benzyl alcohol. Yield: 73%. M.p. 112–114° C. Compound 16.

Endo 3-(3-[4-(3-methoxyphenyl)-3-butyn-2-yloxy]-1,2,5-thiadiazol-4-yloxy)-1-azabicyclo[2.2.1]heptane, oxalate from endo 3-(3-propylsulfonyl-1,2,5-thiadiazol-4-yloxy)-1-azabicyclo[2.2.1]heptane (example 3) and 4-(3-methoxyphenyl)-3-butyn-2-ol. Yield: 62%. M.p. 102–103° C. Compound 17.

Endo 3-(3-[3-(4-chlorophenyl)-2-propynyl-1-oxy]-1,2,5-thiadiazol-4-yloxy)-1-azabicyclo[2.2.1]heptane, oxalate from endo 3-(3-propylsulfonyl-1,2,5-thiadiazol-4-yloxy)-1-azabicyclo[2.2.1]heptane (example 3) and 3-(4-chlorophenyl)-2-propyn-1-ol. Yield: 40%. M.p. 118–122° C. Compound 18.

Endo 3-(3-[1-(3-methoxyphenyl)-1-pentyn-3-yloxy]-1,2,5-thiadiazol-4-yloxy)-1-azabicyclo[2.2.1]heptane, oxalate from endo 3-(3-propylsulfonyl-1,2,5-thiadiazol-4-yloxy)-1-azabicyclo[2.2.1]heptane (example 3) and 1-(3-methoxyphenyl)-1-pentyn-3-ol. Yield: 25%. M.p. 98–101° C. Compound 19.

Endo 3-(3-(3-(3-trifluoromethylphenyl)-2-propynyl-1-oxy)-1,2,5-thiadiazol-4-yloxy)-1-azabicyclo[2.2.1]heptane, oxalate from endo 3-(3-propylsulfonyl-1,2,5-thiadiazol-4-yloxy)-1-azabicyclo[2.2.1]heptane (example 3) and 3-(3-trifluoromethylphenyl)-2-propyn-1-ol. Yield: 73%. M.p. 131–135° C. Compound 20.

Endo (Z)-3-(3-(5-(4-fluorophenyl)-3-methyl-2-penten-4-yn-1-yloxy)-1,2,5-thiadiazol-4-yloxy)-1-azabicyclo[2.2.1]heptane from endo 3-(3-propylsulfonyl-1,2,5-thiadiazol-4-yloxy)-1-azabicyclo[2.2.1]heptane, oxalate (example 3) and (Z)-5-(4-fluorophenyl)-3-methyl-2-penten-4-yn-1-ol. Yield: 44%. M.p. 174–177° C. Compound 21.

Endo (E)-3-(3-(5-(4-fluorophenyl)-3-methyl-2-penten-4-yn-1-yloxy)-1,2,5-thiadiazol-4-yloxy)-1-azabicyclo[2.2.1]heptane from endo 3-(3-propylsulfonyl-1,2,5-thiadiazol-4-yloxy)-1-azabicyclo[2.2.1]heptane (example 3) and (E)-5-(4-fluorophenyl)-3-methyl-2-penten-4-yn-1-yloxy). Yield 57%. M.p. 82–84° C. Compound 22.

Endo 3-(3-(3-pyridyl)-2-propyn-1-yloxy)-1,2,5-thiadiazol-4-yloxy)-1-azabicyclo[2.2.1]heptane, dioxalate from endo 3-(3-propylsulfonyl-1,2,5-thiadiazol-4-yloxy)-1-azabicyclo[2.2.1]heptane (example 3) and (3-pyridyl)-2-propyn-1-ol. Yield: 48%. M.p. 136–139° C. Compound 23.

Endo (E/Z)-3-(3-(5-(4-fluorophenyl)-2-penten-4-yn-1-yloxy)-1,2,5-thiadiazol-4-yloxy)-1-azabicyclo[2.2.1] heptane from endo 3-(3-propylsulfonyl-1,2,5-thiadiazol-4-yloxy)-1-azabicyclo[2.2.1]heptane, oxalate (example 3) and 5-(4-fluorophenyl)-2-penten-4-yn-1-ol. Yield. 9%. M.p. 185–188° C. Compound 24.

Endo 3-(3-(2-pyridyl)-2-propyn-1-yloxy)-1,2,5-thiadiazol-4-yloxy)-1-azabicyclo[2.2.1]heptane, dioxalate from endo 3-(3-propylsulfonyl-1,2,5-thiadiazol-4-yloxy)-1-azabicyclo[2.2.1]heptane (example 3) and (2-pyridyl)-2-propyn-1-ol. Yield 34%. M.p. 158–160° C. Compound 25.

Endo 3-(3-(3-(3-furyl)-2-propyn-1-yloxy)-1,2,5-thiadiazol-4-yloxy)-1-azabicyclo[2.2.1]heptane, oxalate from endo 3-(3-propylsulfonyl-1,2,5-thiadiazol-4-yloxy)-1-azabicyclo[2.2.1]heptane (example 3) and 3-(3-furyl)-2-propyn-1-ol. Yield 72%. M.p. 146–148° C. Compound 26.

Endo 3-(3-(2,2,3,3,4,4,4-heptafluorobutyl-1-oxy)-1,2,5-thiadiazol-4-yloxy)-1-azabicyclo[2.2.1]heptane, oxalate from endo 3-(3-propylsulfonyl-1,2,5-thiadiazol-4-yloxy)-1-azabicyclo[2.2.1]heptane (example 3) and 2,2,3,3,4,4,4-heptafluorobutan-1-ol. Yield 73%. M.p. 128–131° C. Compound 27.

Endo 3-(3-(3-(3-fluorophenyl)-2-propyn-1-yloxy)-1,2,5-thiadiazol-4-yloxy-1-azabicyclo[2.2.1]heptane, oxalate from endo 3-(3-propylsulfonyl-1,2,5-thiadiazol-4-yloxy)-1-azabicyclo[2.2.1]heptane (example 3) and 3-(3-fluorophenyl)-2-propyn-1-ol. Yield: 84%. M.p. 175–177° C. Compound 28.

EXAMPLE 6

Endo 3-(3-(3,3,3-trifluoropropylthio)-1,2,5-thiadiazol-4-yloxy)-1-azabicyclo-[2.2.1]heptane, oxalate A solution of endo 3-(3-propylsulfonyl-1,2,5-thiadiazol-4-yloxy)-1-azabicyclo[2.2.1]heptane (example 3) (300 mg, 0.76 mmol) and potassium carbonate (210 mg, 1.52 mmol) in DMF (10 ml) was added sodium hydrosulphide (225 mg, 3.00 mmol) under $N_2$. The solution was stirred at 80–100° C. for 4 h. The solution was then cooled to room temperature and added potassium carbonate (1.05 g, 7.6 mmol) and 3,3,3-trifluoropropyl iodide (510 mg, 228 mmol). After 10 min. ice-water and 6N HCl were added to pH 2.0. The aqueous phase was washed with ether (3×), then made basic with NaOH to pH 11.0. The product was extracted with ether (3×), dried ($MgSO_4$) and the solvent evaporated. The residue was taken up in acetone and the product precipitated with oxalic acid in acetone followed by ether to give 230 mg (72%) of the title compound. M.p. 186–1 87° C. Compound 29.

EXAMPLE 7

The following compounds were made in exactly the same manner as described in example 6 by using the reagents indicated.

Endo 3-(3-(4,4,4-trifluorobutylthio)-1,2,5-thiadiazol-4-yloxy)-1-azabicyclo-[2.2.1]heptane, oxalate from endo 3-(3-propylsulfonyl-1,2,5-thiadiazol-4-yloxy)-1-azabicyclo[2.2.1]heptane (example 3) and trifluorobutyl bromide. Yield: 61%. M.p. 114–115° C. Compound 30.

Endo 3-(3-[4-cyanobenzylthio]-1,2,5-thiadiazol-4-yloxy)-1-azabicyclo-[2.2.1]heptane, oxalate from endo 3-(3-propylsulfonyl-1,2,5-thiadiazol-4-yloxy)-1-azabicyclo[2.2.1]heptane (example 3) and 4-cyanobenzyl bromide. Yield: 15%. M.p. 196–197° C. Compound 31.

Endo 3-(3-[2-cyanoethylthio]-1,2,5-thiadiazol-4-yloxy)-1-azabicyclo-[2.2.1]heptane, oxalate from endo 3-(3-propylsulfonyl-1,2,5-thiadiazol-4-yloxy)-1-azabicyclo[2.2.1]heptane (example 3) and 3-bromopropionitrile. Yield: 42%. M.p. 168–169° C. Compound 32.

Endo 3-(3-[2,4-difluorobenzylthio]-1,2,5-thiadiazol-4-yloxy)-1-azabicyclo-[2.2.1]heptane, oxalate from endo 3-(3-propylsulfonyl-1,2,5-thiadiazol-4-yloxy)-1-azabicyclo[2.2.1]heptane (example 3) and 2,4-difluorobenzyl bromide. Yield: 67%. M.p. 98–100° C. Compound 33.

Endo 3-(3-[2-fluoroethyl-1-thio]-1,2,5-thiadiazol-4-yloxy)-1-azabicyclo-[2.2.1]heptane, oxalate from endo 3-(3-butylsulfonyl-1,2,5-thiadiazol-4-yloxy)-1-azabicyclo[2.2.1]heptane (example 8) and 1-bromo-2-fluoroethane. Yield: 59%. M.p. 131–133° C. Compound 34.

EXAMPLE 8

The following compound was made in the same manner as described in example 3 by using the reagents indicated.

Endo 3-(3-butylsulfonyl-1,2,5-thiadiazol-4-yloxy)-1-azabicyclo[2.2.1]heptane, oxalate from endo 3-(3-butylthio-1,2,5-thiadiazol-4-yloxy)-1-azabicyclo[2.2.1]

heptane (example 1). Yield: 94%. M.p. 135–137° C. Compound 35.

EXAMPLE 9

Endo 3-(3-[3-(3-thienyl)-2-propyn-1-yloxy]-1,2,5-thiadiazol-4-yloxy)-1-azabicyclo[2.2.1]heptane, oxalate a) To a suspension of bis(triphenylphosphine)-palladium (II) chloride (300 mg, 0.42 mmol) and copper (I) iodide (100 mg, 0.50 mmol) in diisopropylamine (100 ml) under nitrogen was added 3-bromothiophene (4.9 g, 30 mmol). After reflux under nitrogen for 1.5 h a solution of propargyl alcohol (3.0 g, 33 mmol) in diisopropylamine (50 ml) was added. After reflux for 5 h the reaction mixture was cooled, filtered and concentrated in vacuo. The residue was submitted to flash chromatography using ether/petroleum ether (1:1) as eluent to give 2 g (48%) of 3-(3-thienyl)-2-propyn-1-ol as a crude product.

b) A solution of 3-(3-thienyl)-2-propyn-1-ol (276 mg, 2.0 mmol) and sodium hydride (80%) (90 mg, 3.0 mmol) in dry THF (10 ml) was stirred at room temperature for 1 h under nitrogen. A solution of endo 3-(3-butylsulfonyl-1,2,5-thiadiazol-4-yloxy)-1-azabicyclo[2.2.1]heptane (example 8) (317 mg, 1.0 mmol) in dry THF (5 ml) was added. After 16 h the reaction was quenched with water and THF evaporated off. The product was extracted with ether (3×). The extracts were dried (MgSO$_4$), filtered and the solvent evaporated.

The product was taken up in acetone and precipitated with oxalic acid in acetone to give 123 mg (30%) of the title compound. M.p. 133–136° C. Compound 36.

EXAMPLE 10

Endo 3-(3-[3-(2-thienyl)-2-propyn-1-yloxy]-1,2,5-thiadiazol-4-yloxy)-1-azabicyclo[2.2.1]heptane, oxalate a) To a suspension of tetrakis (triphenylphosphine) palladium (300 mg, 0.25 mmol) and copper (I) iodide (100 mg, 0.50 mmol) in diisopropylamine (100 ml) under nitrogen was added 2-iodothiophene (6.3 g, 30 mmol). After stirring 1.5 h at room temperature a solution of propargyl alcohol (3.0 g, 33 mmol) in diisopropylamine (50 ml) was added. After 16 h at room temperature the mixture was filtered and concentrated in vacuo. The residue was submitted to flash chromatography using dichloromethane as eluent to give 3.0 g (73%) of 3-(2-thienyl)-2-propyn-1-ol as a crude product.

b) A solution of 3-(2-thienyl)-2-propyn-1-ol (276 mg, 2.0 mmol) and sodium hydride (80%) (90 mg, 3.0 mmol) in dry THF (10 ml) was stirred at room temperature for 1 h under nitrogen. A solution of endo 3-(3-butylsulfonyl-1,2,5-thiadiazol-4-yloxy)-1-azabicyclo[2.2.1]heptane (example 8) (317 mg, 1.0 mmol) in dry THF (5 ml) was added. After stirring for 16 h the reaction was quenched with water and THF evaporated off. The product was extracted with ether. The product was precipitated as a HCl salt to give 253 mg (70%) of the title compound. M.p. 180–184° C. Compound 37.

EXAMPLE 11

Endo 3-(3-[1-cyclopropylethyl-1-oxy]-1,2,5-thiadiazol-4-yloxy)-1-azabicyclo[2.2.1]heptane, oxalate A suspension of sodium hydride (50 mg, 1.5 mmol) in dry THF (5 ml) and α-methylcyclopropanemethanol (100 μl, 1.0 mmol) was stirred at room temperature for 1 h. The reaction was then added endo 3-(3-butylsulfonyl-1,2,5-thiadiazol-4-yloxy)-1-azabicyclo[2.2.1]heptane (160 mg, 0.5 mmol) (example 8). After 16 h the reaction was quenched with ice-water, added potassium carbonate and the product extracted with dichloromethane (3×). The extracts were dried (MgSO$_4$) and the solvent evaporated. The product was taken up in acetone and precipitated with oxalic acid in acetone followed by ether to give 145 mg (50%) of the title compound. M.p. 134–137° C. Compound 38.

EXAMPLE 12

The following compounds were made in the same manner as described in example 4 by using the reagents indicated:

Endo 3-(3-[1-(3-methoxyphenyl)-4-methyl-1-pentyn-3-yloxy]-1,2,5-thiadiazol-4-yloxy)-1-azabicyclo[2.2.1]heptane, oxalate from endo 3-(3-butylsulfonyl-1,2,5-thiadiazol-4-yloxy)-1-azabicyclo[2.2.1]heptane (example 8) and 1-(3-methoxyphenyl)-4-methyl-1-pentyn-3-ol. Yield: 35%. M.p. 144–147° C. Compound 39.

Endo 3-(3-[2,2,2-trifluoroethyl-1-oxy]-1,2,5-thiadiazol-4-yloxy)-1-azabicyclo[2.2.1]heptane, oxalate from endo 3-(3-butylsulfonyl-1,2,5-thiadiazol-4-yloxy)-1-azabicyclo[2.2.1]heptane (example 8) and 2,2,2-trifluoroethanol. Yield: 54%. M.p. 153–156° C. Compound 40.

Endo 3-(3-cyclobutylmethyloxy-1,2,5-thiadiazol-4-yloxy)-1-azabicyclo-[2.2.1]heptane, oxalate from endo 3-(3-butylsulfonyl-1,2,5-thiadiazol-4-yloxy)-1-azabicyclo[2.2.1]heptane (example 8) and cyclobutyl methanol. Yield: 46%. M.p. 96–99° C. Compound 41.

Endo 3-(3-[1-(3-fluorophenyl)-4-methyl-1-pentyn-3-yloxy]-1,2,5-thiadiazol-4-yloxy)-1-azabicyclo[2.2.1]heptane, oxalate from endo 3-(3-butylsulfonyl-1,2,5-thiadiazol-4-yloxy)-1-azabicyclo[2.2.1]heptane (example 8) and 1-(3-fluorophenyl)-4-methyl-pent-1-yn-3-ol. Yield: 40%. M.p. 103–105° C. Compound 42.

Endo 3-(3-[1-(4-fluorophenyl)-4-methyl-1-pentyn-3-yloxy]-1,2,5-thiadiazol-4-yloxy)-1-azabicyclo[2.2.1]heptane, oxalate from endo 3-(3-butylsulfonyl-1,2,5-thiadiazol-4-yloxy)-1-azabicyclo(2.2.1]heptane (example 8) and 1-(4-fluorophenyl)-4-methyl-pent-1-yn-3-ol. Yield: 44%. M.p. 128–130° C. Compound 43.

Endo 3-(3-[1-(2-thienyl)-4-methyl-1-pentyn-3-yloxy-]1,2,5-thiadiazol-4-yloxy)-1-azabicyclo[2.2.1]heptane, oxalate from endo 3-(3-butylsulfonyl-1,2,5-thiadiazol-4-yloxy)-1-azabicyclo[2.2.1]heptane (example 8) and 4-methyl-1-thiophen-2-yl-pent-1-yn-3-ol. Yield: 77%. M.p. 121–122° C. Compound 44.

Endo 3-(3-[1-(3-chlorophenyl)-4-methyl-1-pentyn-3-yloxy]-1,2,5-thiadiazol-4-yloxy)-1-azabicyclo[2.2.1]heptane, oxalate from endo 3-(3-butylsulfonyl-1,2,5-thiadiazol-4-yloxy)-1-azabicyclo[2.2.1]heptane, oxalate (example 8) and 1-(3-chlorophenyl)-4-methyl-pent-1-yn-3-ol. Yield: 69%. M.p. 113–115° C. Compound 45.

EXAMPLE 13

The following compounds were made in the same manner as described in example 4 by using the reagents indicated, except that the title compounds were precipitated as tartrate in isopropanol:

Endo 3-(3-[3-(3-chlorophenyl)-2-propynyl-1-oxy)-1,2,5-thiadiazol-4-yloxy]-1-azabicyclo[2.2.1]heptane, tartrate from endo 3-(3-butylsulfonyl-1,2,5-thiadiazol-4-yloxy)-1-azabicyclo[2.2.1]heptane (example 8) and 3-(3-chlorophenyl)-prop-2-yn-1-ol. Yield: 78%. M.p. 148–149° C. Compound 46.

Endo 3-(3-[3-(3,5-difluorophenyl)-2-propynyl-1-oxy]-1,2,5-thiadiazol-4-yloxy)-1-azabicyclo[2.2.1]heptane, oxalate from endo 3-(3-butylsulfonyl-1,2,5-thiadiazol-4-yloxy)-1-azabicyclo[2.2.1]heptane (example 8) and 3-(3,5-difluorophenyl)-prop-2-yn-1-ol. Yield: 98%. M.p. 121–123° C. Compound 47.

EXAMPLE 14

The following compounds were made in the same manner as described in example 13 by using the reagents indicated, except that the title compounds were purified by column chromatography before precipitating as a tartrate:

Endo 3-(3-[1-(2-pyridyl)-4methyl-1-pentyn-3-yloxy)-1,2,5-thiadiazol-4-yloxy)-1-azabicyclo[2.2.1]heptane, tartrate from endo 3-(3-butylsulfonyl-1,2,5-thiadiazol-4-yloxy)-1-azabicyclo[2.2.1]heptane (example8) and 4-methyl 1-(2-pyridyl)-pent-1-yn-3-ol. Yield: 71%. M.p. 101–103° C. Compound 48.

Endo 3-(3-[1-(3,5-dichlorophenyl)-4-methyl-1-pentyn-3-yloxy]-1,2,5-thiadiazol-4-yloxy)-1-azabicyclo[2.2.1]heptane, tartrate from endo 3-(3-butylsulfonyl-1,2,5-thiadiazol-4-yloxy)-1-azabicyclo[2.2.1]heptane (example 8) and 1-(3,5-dichlorophenyl)-4-methyl-pent-1-yn-3-ol. Yield: 48%. M.p. 179–181° C. Compound 49.

Endo 3-(3-[1-(3,5-difluorophenyl)-4-methyl-1-pentyn-3-yloxy]-1,2,5-thiadiazol-4-yloxy)-1-azabicyclo[2.2.1]heptane, tartrate from endo 3-(3-butylsulfonyl-1,2,5-thiadiazol-4-yloxy)-1-azabicyclo[2.2.1]heptane (example 8) and 1-(3,5-difluorophenyl)-4-methyl-pent-1-yn-3-ol. Yield: 40%. M.p. 158–160° C. Compound 50.

Endo 3-(3-[3-(2-thiazolyl)-2-propyn-1-yloxy]-1,2,5-thiadiazol-4-yloxy)-1-azabicyclo[2.2.1]heptane, tartrate from endo 3-(3-butylsulfonyl-1,2,5-thiadiazol-4-yloxy)-1-azabicyclo[2.2.1]heptane (example 8) and 3-(thiazolyl)-2-propyn-1-ol. Yield: 22%. M.p. 114–116° C. Compound 51.

What is claimed is:

1. A compound of formula I or the quaternized form thereof:

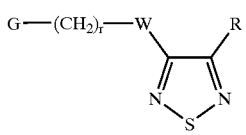

(I)

wherein

W is oxygen or sulphur;

R is $-OR^4$, $-SR^4$, $-SOR^4$, $-SO_2R^4$, or $R^4$, wherein $R^4$ is propynyl substituted with phenoxy, wherein the phenoxy is optionally substituted with one or more halogen(s), $-OH$, $-NO_2$, $-CN$, $C_{1-4}$-alkyl, $C_{1-4}$-alkylthio, $C_{1-4}$-alkoxy, $-SCF_3$, $-OCF_3$, $-CF_3$, $-CONH_2$ or $-CSNH_2$;

r is 0, 1 or 2; and

G is an azabicyclic ring system which is:

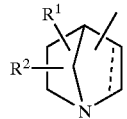

(G)

wherein the thiadiazole ring is attached at any appropriate position;

$R^1$ and $R^2$ independently are hydrogen, $-OH$, $=O$, $C_{1-15}$-alkyl, $C_{2-15}$-alkenyl, $C_{2-15}$-alkynyl, $C_{1-10}$-alkoxy, and $C_{1-5}$-alkyl substituted with one or more halogen(s), $-OH$, $-COR^8$, $-CH_2OH$, $-NH_2$, carboxy and phenyl;

$R^8$ is hydrogen, or $C_{1-6}$-alkyl;

⋯ is a single or double bond;

or a pharmaceutically acceptable salt or solvate thereof.

2. A compound of claim 1, wherein G is saturated.

3. A compound of claim 1, wherein G is

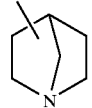

(G)

and wherein the $-(CH_2)_r-$W-thiadiazole is attached to the 3- or 4-position of G.

4. A compound of claim 1 wherein G is

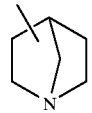

(G)

5. A compound of claim 1 wherein r is 0.

6. A compound of claim 1 wherein W is oxygen.

7. A compound of claim 1 wherein $R^4$ is 2-propyn-1-yl.

8. A pharmaceutical composition comprising a compound of claim 1 together with one or more pharmaceutical acceptable carriers or diluents.

9. The pharmaceutical composition of claim 8, wherein said dosage unit comprises from about 0.1 to about 100 mg of the compound.

10. A method of treating a disease in the central nervous system caused by malfunctioning of the muscarinic cholinergic system comprising administering to a subject in need thereof a pharmaceutically effective amount of a compound of claim 1.

* * * * *